United States Patent
Clothier (12)

(10) Patent No.: US 6,852,503 B1
(45) Date of Patent: Feb. 8, 2005

(54) COMPOSITIONS AND METHODS FOR UTILIZING MIXED SUBSTRATE SOLUTIONS OF LUMINOLS AND DIOXETANES

(75) Inventor: Caroline Clothier, Winnebago, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 419 days.

(21) Appl. No.: 10/157,757

(22) Filed: May 29, 2002

Related U.S. Application Data

(60) Provisional application No. 60/294,511, filed on May 30, 2001.

(51) Int. Cl.$^7$ .................................................. C12Q 1/28
(52) U.S. Cl. .............................. 435/28; 435/4; 435/21; 252/700; 436/172
(58) Field of Search ................................. 435/28, 21, 4; 252/700; 436/172

(56) References Cited

U.S. PATENT DOCUMENTS

| | | | | |
|---|---|---|---|---|
| 4,729,950 A | * | 3/1988 | Kricka et al. | 435/28 |
| 5,242,842 A | * | 9/1993 | Sundrehagen | 436/536 |
| 5,582,775 A | * | 12/1996 | Akhavan-Tafti | 252/700 |
| 5,994,073 A | * | 11/1999 | Bronstein et al. | 435/6 |
| 6,068,979 A | * | 5/2000 | Akhavan-Tafti | 435/6 |

* cited by examiner

Primary Examiner—Leon B. Lankford, Jr.

(57) ABSTRACT

A dual enzyme chemiluminescent substrate formulation useful for the independent or simultaneous analysis of the enzymes is disclosed, the formulation includes, as one substrate component, dihydrophthalazinedione, such as luminol or isoluminol, and a peroxide source and, as the other substrate component, a 1,2-dioxetane. The formulation further includes a polymeric quaternary onium salt as an isolating agent to defeat adverse interactions between the substrate pairs.

5 Claims, 3 Drawing Sheets

Figure 1:
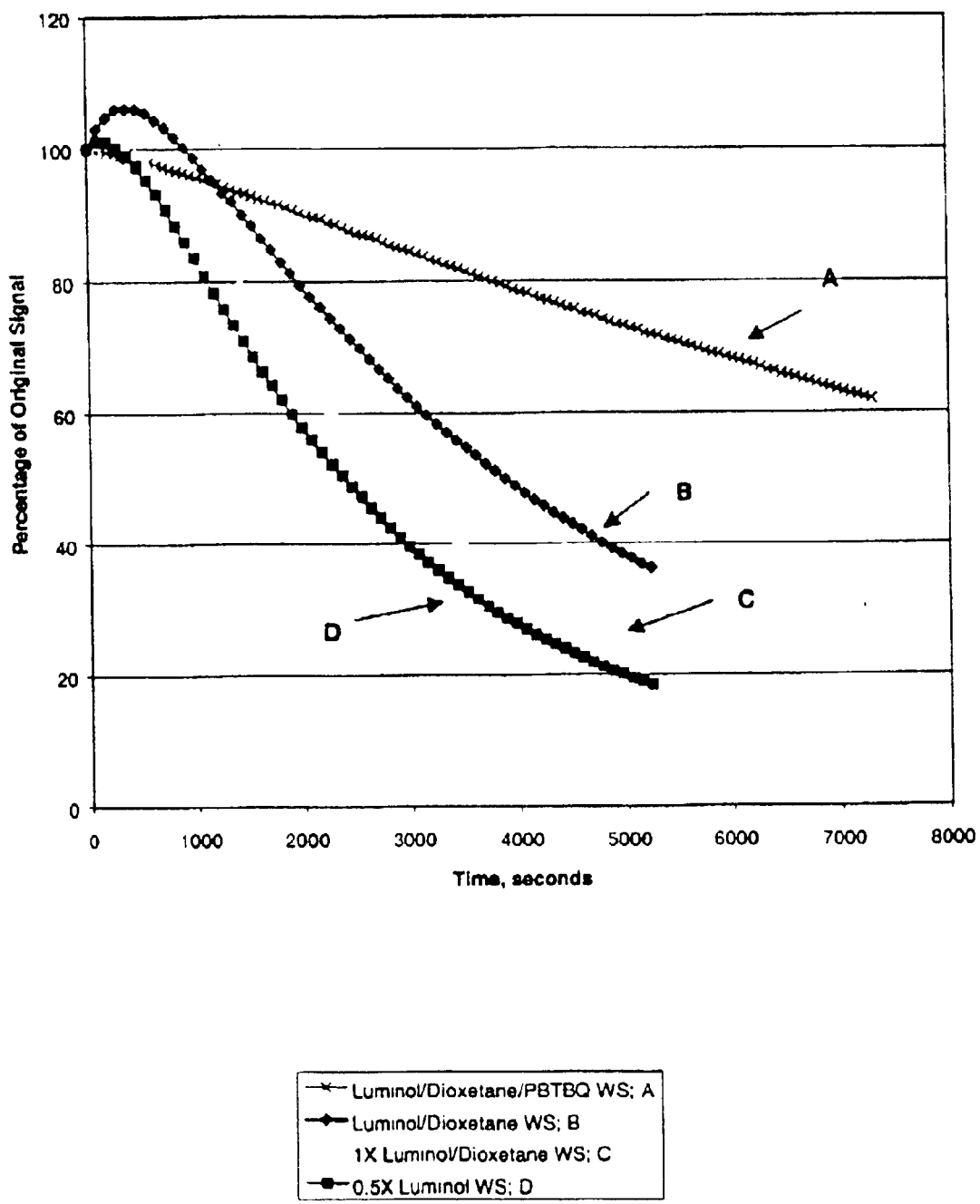

COMPOSITIONS AND METHODS FOR UTILIZING MIXED SUBSTRATE SOLUTIONS OF LUMINOLS AND DIOXETANES

RELATED APPLICATION

This application claims priority from provisional patent application Ser. No. 60/294,511, filed May 30, 2001.

FIELD OF INVENTION

The present invention relates to enzyme mediated chemiluminescent assay systems and, more particularly, to such systems for assaying the activity of multiple enzymes using a single substrate solution. The invention is especially concerned with chemiluminescent assays for the detection of two analytes using a single novel solution.

BACKGROUND OF INVENTION

Chemiluminescent detection of analytes of synthetic or natural origin such as proteins or nucleic acids, as well as other biologic molecules, is a popular assay method. Currently available chemiluminescent systems are sensitive and are not accompanied by the safety drawbacks associated with radioactive detection.

In one such assay, luminescence is achieved by the oxidation of a luminol or isoluminol substrate solution in the presence of an oxidizing agent such as hydrogen peroxide or hydrogen peroxide source, such as perborate, and a peroxidase catalyst, such as horseradish peroxidase (HRP). Another assay is based on the use of a solution containing, as a substrate, a phosphate ester of a 1,2-dioxetane. A chemiluminescent signal (commonly referred to as relative light units, RLU) is elicited by action of phosphatase on the substrate. These assays systems have been primarily practiced as independent methods using separate substrate solutions for the determination of either peroxidase or phosphatase activity, exceptions being those examples noted immediately below.

The utility of enzyme substrate formulations for the detection of multiple enzymes has been recognized previously with respect to the provision of a commodity item serving an either/or purpose. For example, Vector Laboratories sells a chemiluminescent substrate formulation for the determination of alkaline phosphatase (AP) or peroxidase activity called DuoLux based on Lumigen's APS-5 acridan substrate for phosphatase and another substrate for peroxidase. While this formulation may be employed in an either/or situation, the use of the formulation in a combined fashion is not indicated, nor recommended, nor would benefits ascribed to the composition indicate that it would have utility in a combined fashion.

In similar fashion, U.S. Pat. No. 6,068,979 shows a sequential chemiluminescent detection technique for peroxidase and alkaline phosphatase utilizing a dioxetane compound for phosphatase activity and an alkylacridan-9-carboxylate derivative for peroxidase activity. This patent, however, does not show the simultaneous detection of the two enzymes, nor does the patent indicate any synergistic advantages of the formulation in its use in a combined fashion.

It would be desirable to have a single substrate solution that could be used interchangeably in a separate as well as in a combined fashion with either of the two enzymes.

SUMMARY OF INVENTION

In accordance with the present invention, there is provided an improved dual enzyme chemiluminescent substrate formulation. The use of the dual enzyme substrate formulation provided by this invention allows for the measurement, using a single solution, of two or more analytes simultaneously or independently.

The formulation of the present invention comprises, as one substrate component, a dihydrophthalazinedione and a peroxide source, e.g., a luminol (luminol or isoluminol) and hydrogen peroxide or sodium perborate, and, as the other substrate component, a 1,2-dioxetane. Together with the forgoing substrates, and for the purpose of realizing the advantages provided by this invention, there is also included in the formulation a polymeric quaternary onium salt. This salt serves as an isolating agent to defeat adverse interactions between the two enzyme-substrate pairs, thus permitting independent or simultaneous analysis. These adverse interactions can include (1) degradation, by peroxidase, of the light emitting phenolate intermediate species produced by the normal enzymatic catalysis of the dioxetane and its enzyme and/or (2) apparent loss of peroxidase activity through competitive inhibition of luminol turnover effected by the phenolate intermediate species.

DESCRIPTION OF INVENTION

Turning to the substrate pairs, these are well known enzyme substrates. A luminol is conventionally used as a substrate for a peroxidase and provides a peroxidase-specific chemiluminescent signal. The second substrate, the 1,2 dioxetane, provides a chemiluminescent signal from a specific enzyme other than peroxidase, such as a phosphatase. In practicing the present invention, these substrates are used in the formulation in amounts as are conventional in assaying for the respective enzymes.

As indicated, the formulation of the present invention includes, as an isolating agent, a polymeric quaternary onium salt. Examples of useful salts are poly (vinylbenzyltributyl ammonium chloride)(TBQ) and poly (vinylbenzyldimethylbenzyl ammonium chloride) (BDMQ). The salt is included in the formulation in an amount sufficient to defeat the adverse interactions identified above which can prevent the advantages of the present invention from being realized. Typically, the salt can be included in the formulation in an amount of about 0.001%–50% w/v and generally at least about 0.1%.

In addition to the above salts, other examples of isolating agents that can be used herein are the quaternary onium salts identified in U.S. Pat. No. 5,994,073. Therein, along with TBQ and BDMQ, the salts are disclosed as dioxetane enhancer agents. The disclosure of this patent is herein incorporated by its reference in its entirety.

Preferred commercially available quaternary onium salts are Nitro-Block and Nitro-Block II available from Tropix, Inc. Other useful isolating agents are the polymeric phosphonium salts described in U.S. Pat. Nos. 5,474,725 and 5,582,775, the disclosures of which are hereby incorporated herein by reference in their entirety.

The novel enzyme substrate formulation provided by this invention allows for the measurement, using a single substrate solution, of two or more analytes simultaneously or independently. The solution can be used where (1) in order to achieve resolution between analytes, it is necessary that the chemiluminescent emissions from the respective substrates possess different emission profiles or where (2) resolution between analytes is not necessary, but where the total amount of the emitted light attributable to the combined presence of multiple analytes is required to be measured with confidence as the summation of the individual activities.

The first of the above situations may arise where two or more distinct antibodies labeled with different enzymes are to be detected. The latter is most applicable where the total detection of a class of substances is beneficial. The use of the formulation of this invention is especially adaptable to solution assay formats such as ELISA assays since methods are provided for the resolution of different entities without reliance on spatial separation as can be employed in blotting applications. The invention, however, also finds utility in blotting applications.

The distinct and unexpected advantages achieved by practicing the present invention involving the inclusion of an isolating agent are as follows: (1) the signal provided from the dioxetane component of the mixture is comparable to that obtained using the dioxetane substrate alone, this in spite of the fact that there is present in the solution an oxidizing agent necessary for the accompanying peroxidase activity; (2) the combined activity of the simultaneous reactions of the luminol/peroxidase pair and the dioxetane/enzyme pair are isolated to prevent interfering interactions between the enzyme-substrate pairs to allow for capture of the full signal of the independent enzymes; and (3) the signal provided from the luminol/peroxidase pair has an increased chemiluminescent half-life. Furthermore, by appropriate selection of an enhancer of the peroxidase activity, the observed activity (i.e. signal output) from the dioxetane can be enhanced, while still providing for enhancement of peroxidase activity.

A further advantage that can be achieved in combination with the heretofore identified advantages is the detection of concurrent enzyme activities from different enzyme-substrate pairs. This can be achieved by the selection of a dioxetane capable of generating a luminescent signal with substantially differing emission spectra from that of the dihydrophthalazinedione compound. The signal from the two different enzymes can be resolved and therefore, simultaneously or sequentially measured, and thereby constituting a multiplexed assay, by employing the use of appropriate optical filters to isolate each substrate's emission profile.

As indicated a Luminol/Peroxide substrate for assaying peroxidase activity is a component of the formulation of this invention. In order to obtain useful levels of luminescence (e.g., detectable levels) using this substrate, a luminescent enhancer is also present during oxidation of the substrate. Among the enhancers which have been successfully used with peroxidases are aromatic amines (U.S. Pat. No. 4,729,950), phenols (U.S. Pat. No. 4,598,044), and azines (e.g., phenothiazines, phenoxazines) and phenolindophenols (U.S. Pat. No. 5,171,668); the disclosures in all of which patents are incorporated herein by reference in their entirety.

In PCT/US97/06422 an improved method is provided for the chemiluminescent assay of peroxidase activity using a Luminol/Peroxide Substrate generally useful in connection with the detection of analytes of all types (e.g., biological macromolecules, organic molecules, natural or synthetic molecules, etc). The disclosure of this PCT application is incorporated herein by reference in its entirety. The method disclosed is particularly applicable to detection of proteins and nucleic acids using all types of membrane-based assays by techniques such as dot blotting, western blotting, southern blotting, and northern blotting, colony filter, hybridization, etc. Furthermore, the invention is particularly applicable to the detection of analytes using all types of solution-based, luminometric assays, such as ELISAs (Enzyme Linked Immunoabsorbent Assays), coated tube assays, bead assays, etc.

In the referenced PCT application, luminescence is developed more rapidly than previously reported, and the intense luminescence persists for a period of time comparable to the chemiluminescent substrate system based on 1,2 dioxetanes. Thus, by using the method disclosed therein rapid development of a high intensity luminescence is achieved and said luminescence is of an extended duration. Preferred luminol/peroxide substrate systems are sold by Pierce Chemical Company, Rockford, Ill., under the trademark SuperSignal®.

The improvement in the SuperSignal® substrate formulations is achieved by using, as the enhancer, azines such as the phenothiazines or phenoxazines free of specific classes of compounds which adversely affect the performance of the entire system, and which have been found to be present in previous enhancer compositions. These compounds, which must be reduced in concentration from their levels in conventional enhancer preparations are azines in which the nitrogen atom of the azine ring has a hydrogen bonded directly thereto. It is also preferred to provide aqueous solutions of the substrate, oxidizing agent, and enhancer by using peroxidase enhancers which contain a water-solubilizing substituent such as that provided by a covalently attached alkyl sulfonate salt, substituted ammonium salt, or phosphonium salt. A preferred azine enhancer disclosed for use in this PCT application is the sodium salt of N-propylsulfonate phenothiazine.

In one aspect of the present invention, it has been found that the inclusion of the enhancers identified in the above referenced PCT application as being useful for enhancement for luminol/peroxidase assays also provides for further enhancement of luminescence from 1,2-dioxetanes. Importantly, the enhancement of luminescence from the 1,2-dioxetane with the enhancer still allows for accompanying enhancement of the peroxidase enzyme when the two enzymes are concurrently assayed.

In practicing the present invention, a semi-opaque flocculent may be created when including in the substrate solution the preferred azine enhancer as described above in the aforementioned PCT application. This flocculation does not prevent the realization of the advantages of this invention heretofore identified, but may be unacceptable in a commercial formulation. The nature of the flocculation is believed to occur due to interaction of the negatively charged sulfonate group on the peroxidase enhancer and the positively charged groups on the polymeric quaternary onium salt isolating agent. Other known peroxidase enhancers which do not contain the sulfonate group can be used where flocculation is to be avoided.

Turning to the other necessary substrate component of the present dual enzyme substrate formulation, i.e., the dioxetane-based substrate, a wide variety of such are disclosed in U.S. Pat. No. 5,994,073, identified previously, and also in U.S. Pat. No. 5,112,960, as well as the patents and applications referenced therein, the disclosures of which are all hereby incorporated by reference in their entireties. In these references, modification of the dioxetane via esterification with an appropriate group imparts specificity towards a particular enzyme. For example, the phosphate ester of the dioxetane allows for the dioxetane to serve as a phosphatase substrate. Cleavage of the phosphate ester gives rise to a metastable intermediate, a labile oxyanion of the dioxetane is formed, which leads to chemiluminescence. The oxyanion itself is the light generating species.

Preferred 1,2-dioxetanes are stabilized by the addition of a stabilizing group to at least one of the carbon molecules of the dioxetane ring. An exemplary stabilizing group is spiro-bound adamantane. Such dioxetanes can be further substituted at the other carbon position with an aryl moiety, preferably phenyl or naphthyl, the aryl moiety being substituted by an oxygen which is in turn bound to an enzyme-labile group. Examples of such commercially available dioxetanes include CDP-Star, CSPD, Galacton, Glucuron, and NA-Star from Tropix, Inc. U.S. Pat. Nos. 4,952,707 and 4,931,223 assigned to Tropix, Inc. provide examples of 1,2-dioxetanes capable of having varied spectral emission profiles.

As noted above, it has been previously recognized that the addition of water-soluble polymeric onium salts to the aqueous sample improves or enhances chemiluminescence of 1,2-dioxetanes. U.S. Pat. No. 5,654,154 recognizes that this enhancement is achieved, at least in part, through the formation of hydrophobic regions in which the dioxetane oxyanion is sequestered. Decomposition in these hydrophobic regions enhances chemiluminescence, because water-based light quenching reactions are suppressed. Among the recognized water-soluble quaternary polymer salts employed, TBQ provides unexpectedly superior enhancement, through this hydrophobic region-forming mechanism.

The patent goes on to recognize that the chemiluminescent enhancement achieved by the addition of water-soluble polymeric quaternary polymer salts can be further improved by the inclusion, in the aqueous sample, of an additive, which improves the ability of the quaternary polymeric salt to sequester the dioxetane oxyanion and the resulting excited state emitter reporting molecule in a hydrophobic region. Thus, the combination of the polymeric quaternary salt and the additive, together, produce an increase in enhancement far beyond that produced separately.

In formulating the dual substrate solution of this invention, sufficient concentrations of the active ingredients in the respective substrates for peroxidase and phosphatase are necessary for signal generation. The relative signal of each enzyme can be modified for a given particular character by varying these concentrations. Formulations optimized for activity of either the phosphatase or peroxidase enzyme independently are easily obtained by routine procedures known to those skilled in the art. Examples of optimized formulations for peroxidase and phosphatase substrate solutions independently have been given in the previously cited patents and applications.

In like fashion, the concentration of the isolating agent may be varied, with the optimum concentration being the minimum required to defeat adverse interactions among the enzyme-substrate pairs. Useful concentration ranges of the onium salts disclosed as phosphatase activity enhancers as shown in the previously cited patents are considered useful in practicing the present invention.

The following Examples illustrate the present invention.

EXAMPLE I
Preparation of a Luminol/Dioxetane Working Solution Devoid of Onium Salt SuperSignal® ELISA Pico Chemiluminescent Substrate (Pierce Product No. 37070) Working Solution for peroxidase activity was prepared according to manufacturer's directions by mixing equal volumes of Pico Stable Peroxide Solution and Pico Luminol/Enhancer Solution. Just prior to use in the assay, the Working Solution was mixed in equal volumes with CDP Star Solution (Tropix Product No. MS100) a dioxetane substrate for phosphatase to give a Luminol/Dioxetane Working Solution. The solution does not contain the polymeric quaternary onium salt isolating agent called for by the present invention.

EXAMPLE II
Preparation of Luminol/Dioxetane/PBTBQ (a Polymeric Quaternary Ammonium Salt Isolating Agent) Working Solution SuperSignal® ELISA Pico Working Solution was prepared as in Example I. Just prior to use in the assay, the Pico Working Solution was then mixed in equal volumes with a CDP-Star Solution containing Nitroblock II (Tropix Product No. MS100RN2) to give the Luminol/Dioxetane/PBTBQ Working Solution; the Nitroblock II provides the source of the PBTBQ which is the isolating agent as used in the present invention.

EXAMPLE III
Preparation of Enzyme Dilutions

Calf intestinal alkaline phosphatase (Pierce Product No. 31391) was diluted from an 18.59 mg/ml stock with Tris Buffered Saline/Tween 20 (TBST, 25 mM Tris, 150 mM sodium chloride, pH 7.2, 0.05% Tween 20) to either 3.8 ng/10 µl or 7.5 pg/10 µl. (Note that higher amounts of alkaline phosphatase were employed in examples where this enzyme was not in contact with Nitroblock; higher concentrations of enzyme were required to observe appreciable enzyme activity as compared to the use of lower phosphatase concentrations in the presence of Nitroblock. Horseradish peroxidase (Pierce Product No. 31490) was diluted from a 2 mg/ml stock with TBST to 80 pg/10 µl solution. To form the combined enzyme solutions, equal volumes of the separate phosphatase and peroxidase dilutions were first combined. To the wells of a white opaque 96-well microplate, duplicate 10 µl aliquots of each separate enzyme dilution were added along with 10 µl TBST for a final volume of 20 µl per well. For the combined enzyme solutions, duplicate 20 µl aliquots of the combined solution were added to the wells of the microplate. Blanks containing no enzyme consisted of 20 µl of TBST per well.

EXAMPLE IV
Improved Chemiluminescent Half-life from Luminol by Inclusion of PBTBQ Duplicate peroxidase aliquots (80 pg/10 µl) prepared according to Example III were aliquoted into wells of a white opaque 96-well microplate along with 10 µl of TBST for a final volume of 20 µl per well. The duplicate wells received 100 µl of one of the following formulations: 1)full strength SuperSignal® Pico Working Solution (1×Luminol Working Solution) prepared according to manufacturer's directions, 2) half-strength SuperSignal® Pico Working Solution (0.5×Luminol Working Solution) prepared by diluting the full strength Working Solution one to one with 0.1 M Tris, pH 8.0, 1 mM EDTA, 3) the Luminol/Dioxetane Working Solution described in Example I, or 4) the Luminol/Dioxetane/PBTBQ Working Solution described in Example II. The peroxidase-initiated chemiluminescent signal was measured on a Lumistar Galaxy luminescence plate reader (BMG Laboratories) using a 1 second integration in the case of wells receiving the Luminol/Dioxetane/PBTBQ solution or in the other cases using a Berthold luminescence plate reader with a 0.1 second integration. Measurements were repeatedly obtained with sequential reads of the wells.

FIG. 1 illustrates the results of this experiment by examining the decrease in chemiluminescent signal obtained as a percentage of the original signal versus time. As can be seen, in the absence of PBTBQ, the light output intensity rapidly decreased with time, whereas in the case where PBTBQ was present, over 60% of the original intensity was maintained after 7300 seconds of incubation. As a consequence, the inclusion of PBTBQ serves to decrease the time-dependency of data acquisition in peroxidase assays by minimizing the minute to minute variation in the observed signal intensity. This feature facilitates the ease with which the assay can be utilized in a robotics application. In a separate experiment where the dioxetane was omitted from the combined Luminol/Peroxide/PBTBQ Working Solution, the chemiluminescent half-life of the peroxidase signal was also observed to be increased by the inclusion of the isolating agent as compared to its absence. Consequently, the inclusion of the dioxetane compound is not required to obtain the benefit provided by the isolating agent in improving the observed increase in peroxidase chemiluminescent half-life from the luminol/peroxide enzyme reaction.

EXAMPLE V
Detractive Interaction of Enzyme/Substrate Pairs in the Absence of PBTBQ Duplicate peroxidase aliquots (80 pg/10 µl) prepared according to Example III were aliquoted into wells of a white opaque 96-well microplate along with 10 µl of TBST for a final volume of 20 µl per well. Duplicate phosphatase aliquots (3.8 ng/10 µl) prepared according to Example III were aliquoted into wells of a white opaque 96-well microplate along with 10 µl of TBST for a final volume of 20 µl per well. Duplicates of combined enzyme dilutions were added at 20 µl to give a mixture of 80 pg peroxidase and 3.8 ng phosphatase per well. The duplicate wells received 100 µl of the Luminol/Dioxetane Working Solution (WS) described in Example I. The enzyme-initiated chemiluminescent signal was measured on a LB96V luminescence plate reader (EG&G Berthold) using a 0.1 second integration. Measurements were repeatedly obtained with sequential reads of the wells.

Figure 2:
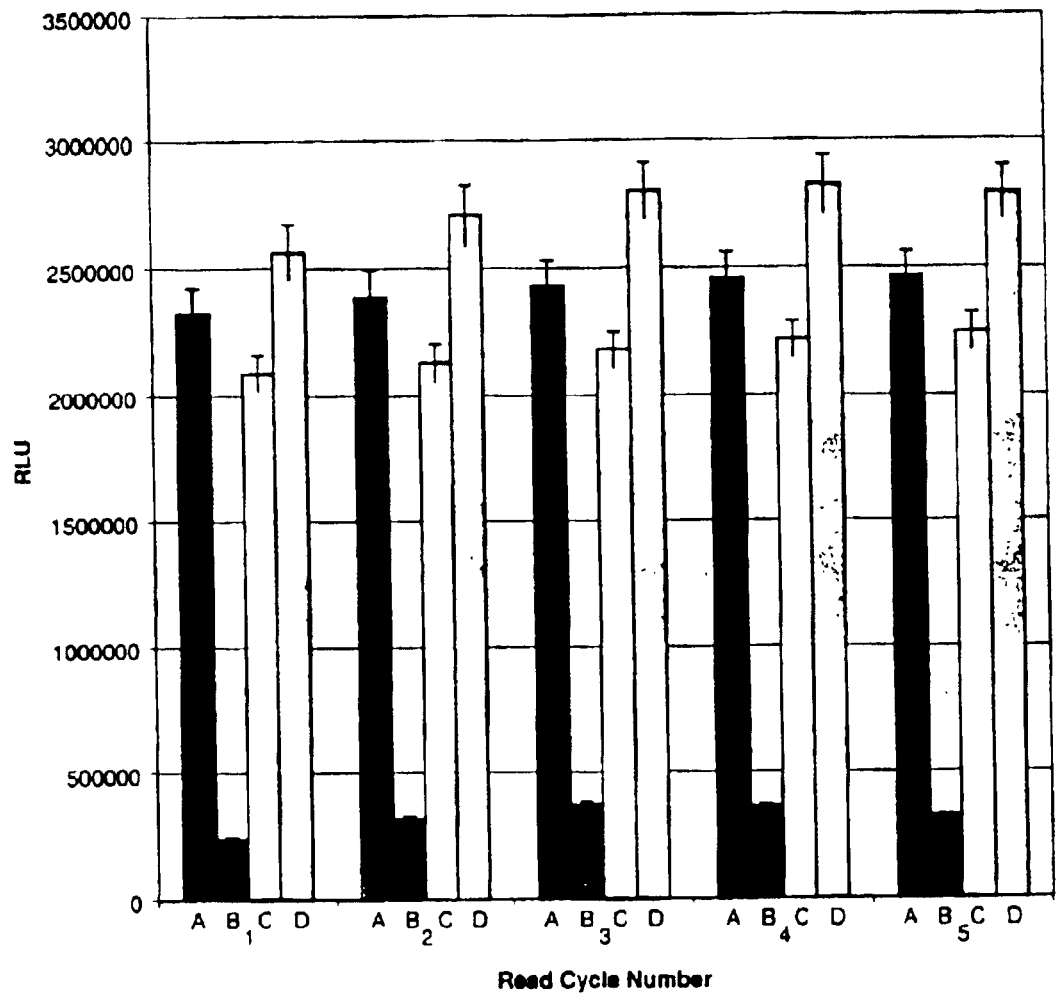
Figure 2:
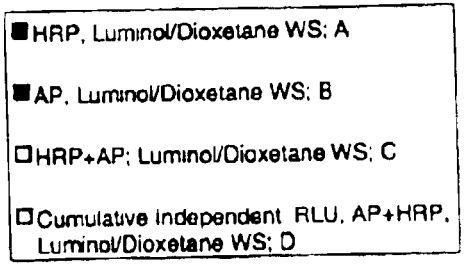

Table I and FIG. 2 illustrate the results of this experiment. While both a peroxidase specific signal and a phosphatase specific signal could be obtained with the Luminol/Dioxetane Working Solution when the two enzymes were measured independently in the absence of the other, the combined presence of alkaline phosphatase and peroxidase without the PBTBQ isolating agent yielded substantially less than the cumulative independent signal of the separately measured signals. The observed signal from the combination of the two enzymes was significantly less than the signal observed from peroxidase when it was measured independently. This phenomenon was observed over several sequential measurements. These results indicate that adverse interactions are taking place among the enzyme-substrate pairs since the chemiluminescent signals are not additive when the two enzymes are in combined presence with the Luminol/Dioxetane Working Solution.

EXAMPLE VI
Elimination of Interfering Interactions of Enzyme/Substrate Pairs by the Use of PBTBQ as an Isolating Agent Duplicate peroxidase aliquots (80 pg/10 µl) prepared according to Example III were aliquoted into wells of a white opaque 96-well microplate along with 10 µl of TBST for a final volume of 20 µl per well. Duplicate phosphatase aliquots (7.5 pg/10 µl) prepared according to Example III were aliquoted into wells of a white opaque 96-well microplate along with 10 µl of TBST for a final volume of 20 µl per well. Duplicates of combined enzyme dilutions were added at 20 µl to give a mixture of 80 pg peroxidase and 7.5 pg phosphatase per well. The duplicate wells received 100 µl of the Luminol/Dioxetane/PBTBQ Working Solution described in Example II. The enzyme-initiated chemiluminescent signal was measured on a LumiStar Galaxy luminescence plate reader (BMG Laboratories) using a 0.1 second integration. Measurements were repeatedly obtained with sequential reads of the wells.

Figure 3:
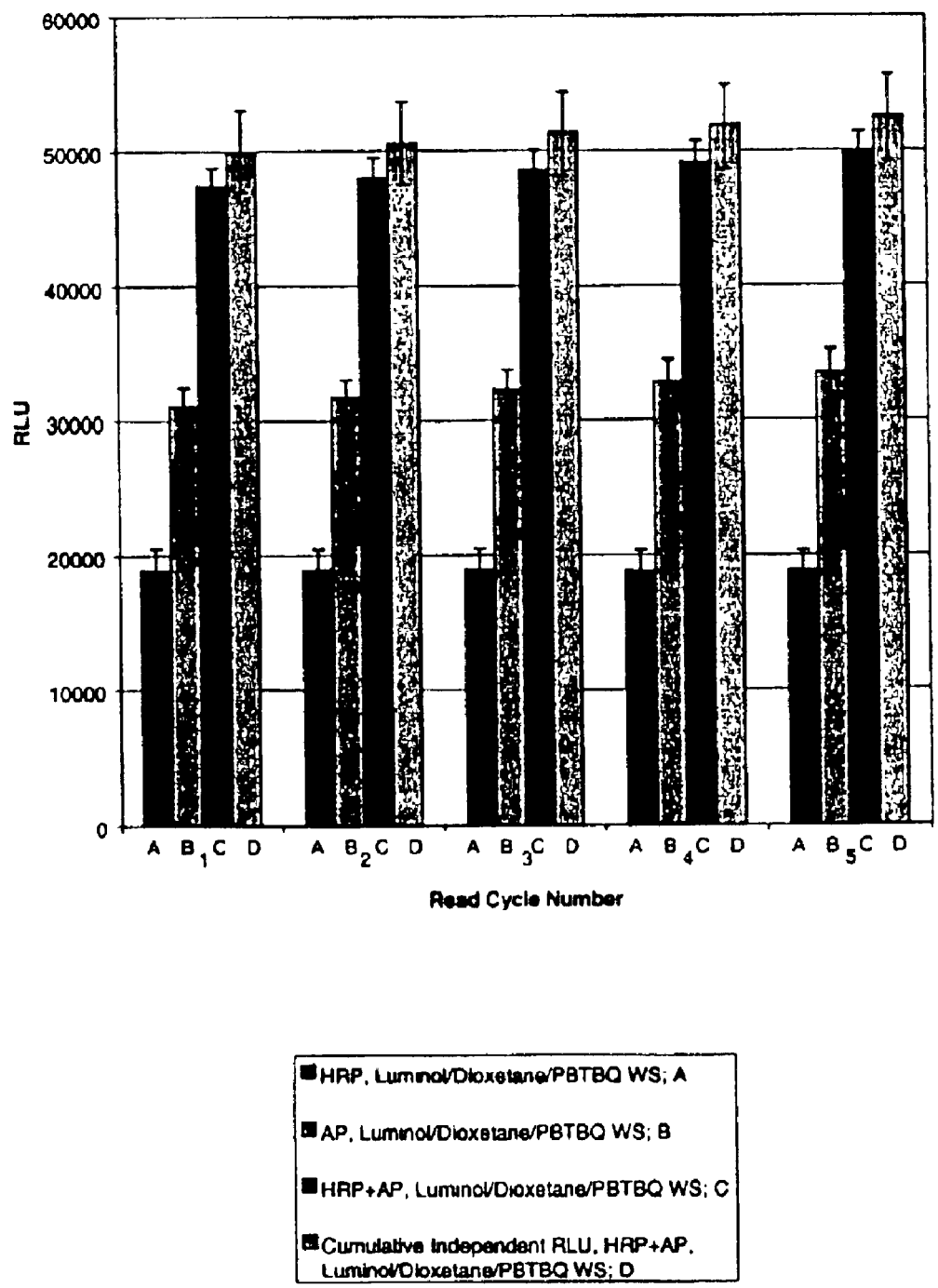

Table II and FIG. 3 illustrate the results of this experiment. Both a peroxidase specific signal and a phosphatase specific signal could be obtained with the Luminol/Dioxetane/PBTBQ Working Solution when the two enzymes were measured independently in the absence of the other. However, the combined presence of alkaline phosphatase and peroxidase yielded a signal essentially identical to the cumulative independent signal of the two separately measured signals. These results indicate that the presence of PBTBQ eliminates the adverse interactions between the enzyme/substrate pairs that would otherwise take place in its absence, as shown in Example V. (Note that instrumentation differences may account for the observed differences in RLU between Examples V and VI, however, the machine-dependency of RLU values is not critical when evaluating the additive nature of the signals on measurements using the same machine conditions.) As a consequence, the total activity of two enzymes in solution can be reliably assessed. Also, by the use of a dioxetane giving a spectral emission capable of being discriminated from the luminol derived spectral emission by the use of appropriate filters, the simultaneous detection of enzymatic activity from a luminol/peroxidase pair and a dioxetane/enzyme pair can be enabled.

TABLE 1

| HRP RLU | AP RLU | HRP + AP RLU | Cumulative HRP + AP RLU |
|---|---|---|---|
| 2327630 +/− 96510 | 239270 +/− 11030 | 2087885 +/− 68375 | 2566900 +/− 107540 |
| 2388200 +/− 105330 | 322110 +/− 11500 | 2129630 +/− 71960 | 2710310 +/− 116830 |
| 2430040 +/− 102560 | 374315 +/− 9025 | 2177720 +/− 72430 | 2804355 +/− 111585 |
| 2457975 +/− 108245 | 369245 +/− 6095 | 2218215 +/− 74135 | 2827220 +/− 114340 |
| 2465045 +/− 101335 | 331550 +/− 3230 | 2249500 +/− 75460 | 2796595 +/− 104565 |

TABLE 2

| HRP RLU | AP RLU | HRP + AP RLU | Cumulative HRP + AP RLU |
|---|---|---|---|
| 18967.5 +/− 1537.5 | 30979.5 +/− 1510.5 | 47323.5 +/− 1467.5 | 49947 +/− 3048 |
| 18937.5 +/− 1539.5 | 31622.5 +/− 1542.5 | 47990 +/− 1497 | 50560 +/− 3082 |
| 18932.5 +/− 1557.5 | 32333.5 +/− 1583.5 | 48581 +/− 1465 | 51266 +/− 3141 |
| 18839.5 +/− 1530.5 | 32983.5 +/− 1625.5 | 49154 +/− 1515 | 51823 +/− 3156 |
| 18790 +/− 1542 | 33660.5 +/− 1649.5 | 49786.5 +/− 1533.5 | 52450.5 +/− 3191.5 |

EXAMPLE IV
Illustration of Useful Peroxidase Enhancers

A variety of known enhancers of peroxidase activity were tested for their effect on the observed alkaline phosphatase activity in a dioxetane formulation containing the PBTBQ alkaline phosphatase enhancement agent. In this experiment, alkaline phosphatase was diluted with Tris Buffered Saline (Pierce BupH Packs) to a concentration of 33.3 pg/10 µl and added to the wells of a white opaque 96-well microplate. 10 µl of TBS served as a background control. 40 mM stock solutions as ws-PT, ws-PT-N-C4-S-C2Cl, and ws-PT Plus (CP-Br) were prepared in water. A 50 mM solution of DMAP was prepared in water. A 20 mM ws-PT Plus (MPA Cl) was prepared in water. 40 mM solutions of MPT and CPPT were prepared in methanol. (See Table 3 for acronym identification of these peroxidase enhancers, some of which are substantially water-soluble(ws).) The control solution was prepared by mixing 2.85 ml of CDP-Star RTU (Tropix Product No. MS100R) with 0.15 ml of NitroBlock II (Tropix Product No. LNX200). For the test solutions, 112 µl of the peroxidase enhancer stock solutions were added to 3 ml of the control solution in the case of the ws-PT, MPT, ws-PT-NC$_4$S, ws-PT-Plus (CP-Br), or CPPT; for the ws-PT-Plus (MPS-C) 224 µl of the stock was added to 3 ml of the control solution; for the DMAP, 150 µl of the stock was added to 3 ml of the control solution; for the test solution containing DMAP and ws-PT, 150 µl of the DMAP stock and 112 µl of the ws-PT stock was added to 3 ml of the control solution. When the test solutions were prepared, a visible flocculation was observed in the case of the ws-PT, MPT, and ws-PT with DMAP test solutions, whereas the other test solutions were observed to remain clear.

To the wells of the microplate containing the alkaline phosphatase aliquots, the control and test formulations were added at 100 µl per well, mixed for approximately one minute, and allowed to react for 30 minutes at which time the chemiluminescent signal was measured on a Berthold EGG Luminometer using a 0.1 second integration time. Table 3 illustrates the relative signal intensities obtained using the response from the control solution set to 100%. The net signal of each solution (background subtracted) was used for these calculations. As can be seen, significant enhancement of the observed phosphatase activity was observed in the case of the ws-PT, MPT, ws-PT-N—C$_4$S—C$_2$—Cl, ws-PT+DMAP formulations whereas the use of the other peroxidase enhancers showed no enhancement of the observed phosphatase activity. Consequently, the relative response factors for alkaline phosphatase and peroxidase activity to each other in the present invention can be modulated by the choice of the peroxidase enhancer used in the substrate solution formulation of this invention.

TABLE 3

| Chemical | Acronym | Response, Percent |
|---|---|---|
| CDP-Star plus Nitroblock II | Control Solution | 100 |
| Sodium (3-phenothiazine-10-yl)-propane-1-sulfonate | ws-PT | 207 |
| 10-methyl-10H-phenothiazine | MPT | 198 |
| Sodium 4-(2-chlorophenothiazin-10-yl)butane-1-sulfonate | ws-PT—N—C$_4$S—C$_2$—Cl | 218 |
| Trimethyl-(3-phenothiazin-10-yl-propyl)ammonium chloride | ws-PT Plus (MPA$^+$Cl$^-$) | 70 |
| [3-(2-chlorophenothiazin-10-yl)-propyl]trimethyl-ammonium bromide | ws-PT Plus (CP—Br$^-$) | 85 |
| 4-(phenothiazin-10-yl)butanoic acid | CPPT | 104 |
| Dimethylamine pyridine | DMAP | 99 |
|  | ws-PT + DMAP | 225 |

I claim:

1. A dual enzyme chemiluminescent substrate formulation useful for the independent or simultaneous analysis of the enzymes comprising, as one substrate component, a dihydrophthalazinedione and a peroxide source and, as the other substrate component, a 1,2-dioxetane, said formulation further including a polymeric quaternary onium salt as an isolating agent to defeat adverse interactions between the substrate pairs.

2. The formulation of claim 1 wherein the dihydrophthalazinedione is a luminol.

3. The formulation of claim 2 wherein the polymeric quaternary onium salt is poly(vinylbenzyltributyl ammonium chloride) or poly(vinylbenzyldimethylbenzyl ammonium chloride).

4. The formulation of claim 3 wherein the polymeric quaternary onium salt is poly(vinylbenzyltributyl ammonium chloride).

5. The formulation of claim 3 wherein the polymeric quaternary onium salt is poly(vinylbenzyldimethylbenzyl ammonium chloride).

* * * * *